United States Patent
Janik

(10) Patent No.: US 10,773,005 B2
(45) Date of Patent: Sep. 15, 2020

(54) MULTI-SENSOR DEVICE

(71) Applicant: B. Braun Avitum AG, Melsungen (DE)

(72) Inventor: Waldemar Janik, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 211 days.

(21) Appl. No.: 16/136,932

(22) Filed: Sep. 20, 2018

(65) Prior Publication Data
US 2019/0091392 A1 Mar. 28, 2019

(30) Foreign Application Priority Data

Sep. 28, 2017 (DE) .......................... 10 2017 122 540

(51) Int. Cl.
*A61M 1/16* (2006.01)
*G01D 11/24* (2006.01)
*G01N 21/31* (2006.01)

(52) U.S. Cl.
CPC ........ *A61M 1/1621* (2014.02); *A61M 1/1609* (2014.02); *A61M 1/1613* (2014.02);
(Continued)

(58) Field of Classification Search
CPC .............. A61M 1/1621; A61M 1/1609; A61M 1/1613; A61M 1/1692; A61M 2205/3306; A61M 2205/3334; A61M 2205/3368; A61M 2205/3317; A61M 2205/3313; A61M 2205/3372; A61M 1/1615; A61M 1/3663; A61M 1/369; A61M 2205/15;
(Continued)

(56) References Cited

U.S. PATENT DOCUMENTS 6,126,831 A 10/2000 Goldau et al.
6,542,761 B1 4/2003 Jahn et al.
(Continued)

FOREIGN PATENT DOCUMENTS

DE 19837667 A1 3/2000
DE 102014012423 A1 2/2016
(Continued)

OTHER PUBLICATIONS

Extended European Search Report for European Application No. 18 196 481.8, dated Feb. 11, 2019, 12 pages 2019.
(Continued)

*Primary Examiner* — Krishnan S Menon
*Assistant Examiner* — Waqaas Ali

(57) ABSTRACT

In a multi-sensor device for a medical apparatus at least one first sensor unit and at least one second sensor unit are arranged at a fluid-guiding line connection along which the sensor units detect at least one variable from a flowing fluid in predetermined proximity to each other in such manner that predetermined signal portions occur and are detectable practically simultaneously in outputs of each of the first and second sensor units. In a method for defining a proximity in said multi-sensor device, positions of the individual sensors are varied in the multi-sensor device and the occurrence of predetermined signal portions is detected in at least two signals detected by the individual sensors, and those positions at which the predetermined signal portions occur practically simultaneously are defined as positions of the proximity.

9 Claims, 2 Drawing Sheets

(52) U.S. Cl.
CPC ......... *A61M 1/1692* (2013.01); *G01D 11/245* (2013.01); *G01N 21/31* (2013.01); *A61B 2560/045* (2013.01); *A61M 2205/3306* (2013.01); *A61M 2205/3313* (2013.01); *A61M 2205/3317* (2013.01); *A61M 2205/3334* (2013.01); *A61M 2205/3368* (2013.01); *A61M 2205/3372* (2013.01)

(58) Field of Classification Search
CPC . A61B 2560/045; G01D 11/245; G01N 21/31
See application file for complete search history.

(56) References Cited

U.S. PATENT DOCUMENTS

| | | |
|---|---|---|
| 6,702,774 B1 | 3/2004 | Polaschegg |
| 2005/0081621 A1 | 4/2005 | Zobel et al. |
| 2011/0009800 A1 | 1/2011 | Dam et al. |
| 2017/0265793 A1 | 9/2017 | Maierhofer |

FOREIGN PATENT DOCUMENTS

| | | |
|---|---|---|
| DE | 102014111732 A1 | 2/2016 |
| EP | 0898974 A2 | 3/1999 |
| EP | 0980686 A2 | 2/2000 |

OTHER PUBLICATIONS

German Search Report for German Application No. 10 2017 122 540.4, dated Apr. 6, 2018, with translation, 15 pages.

MULTI-SENSOR DEVICE

CROSS REFERENCE TO RELATED APPLICATIONS

This application claims priority to German application DE 10 2017 122 540.4 filed Sep. 28, 2017, the contents of such application being incorporated by reference herein.

FIELD OF THE INVENTION

The invention relates to a multi-sensor device for a medical apparatus and especially relates to a multi-sensor device comprising plural individual sensors at an outlet for dialysis fluid, especially used dialysis fluid, of a dialyzer of an apparatus for extracorporeal blood treatment such as a dialysis machine.

BACKGROUND OF THE INVENTION

In extracorporeal blood treatment (e.g. hemodialysis) dialysis fluid flows within a dialyzer around blood of the patient. For determining, for example, the pressure, the temperature, the flow rate of the dialysis fluid, a possible blood leakage, the conductivity, the absorbance and, respectively, extinction or fluorescence of substances usually eliminated with the urine and/or electrolytes and/or the pH value, dialysis machines frequently include plural individual sensors at the outlet for used dialysis fluid of the dialyzer.

Some of said sensors merely constitute safety measures. For example, a sensor serving as blood leakage detector in the event of membrane rupture detects blood flows into the dialysis fluid which have to be detected in due time so as to avoid high blood loss of the patient. Other sensors in turn establish rather uncritical parameters such as the dialysis dose Kt/V. For establishing the dialysis dose Kt/V optical sensors are employed, for example, which measure the absorption of light in the dialysis fluid from which the presence of substances usually to be eliminated with the urine can be concluded. Other methods are based on simultaneous conductivity measurement on the dialysis side upstream and downstream of the dialyzer.

DESCRIPTION OF THE RELATED ART

From prior art optical blood leakage detectors and conductivity probes arranged spatially separately from each other at the outlet for used dialysis fluid are known. It is further known to dispose either an optical sensor at the outlet for used dialysis fluid or to dispose conductivity probes both at the inlet for fresh dialysis fluid and at the outlet for used dialysis fluid to determine the dialysis dose Kt/V. The document DE 10 20 14 012 423 A1, for example, in the context teaches consideration of flow rates to combine time-shifted signals of spatially separated sensors.

The known solutions are detrimental, however, in so far as each of the individual sensors includes a separate housing as well as a separate cable harness and elements for connecting the individual sensors such as tubes, tube clips and the like are required, which results in a large space required. The known solutions furthermore are detrimental due to the design of dead spaces between the individual sensors which are difficult to disinfect. Moreover, it is a drawback that signal losses due to long distances between the individual sensors and mixing or, respectively, thinning and time shift have to be accepted. In addition, for correcting time-shifted signals further parameters such as flow rates and volumes have to be taken into account, which causes increased expenditure.

SUMMARY OF THE INVENTION

Therefore, it is an object underlying the invention to provide a sensor device in which both optical as well as non-optical sensors are combined at the outlet for used dialysis fluid of a dialyzer so that there they require only little space and that data and/or signals supplied by them can be evaluated without any consideration especially of flow-dependent and volume-dependent signal shifts.

According to aspects of the invention, this object is achieved by a multi-sensor device comprising the features of the independent claim. Advantageous further developments of the invention are the subject matter of the attached subclaims.

Consequently, basically a multi-sensor device for a medical apparatus is suggested, comprising
at least one first sensor unit and
at least one n-th/nth sensor unit (10) arranged at a fluid-guiding line connection,
wherein each of the sensor units is arranged to detect at least one measuring value characterizing a physical variable of the fluid flowing through the line connection,
wherein the sensor units are disposed at a maximum spatial distance from each other such that the measuring values detected by said sensor units can be detected at a predetermined maximum time interval.

In other words, the present disclosure is directed to a multi-sensor device for a medical apparatus in which at least one first sensor unit and at least one n-th (meaning one other sensor) sensor unit are arranged at a fluid-guiding line connection along which the sensor units detect at least one variable from a flowing fluid in predetermined proximity to each, wherein a maximum distance between the first sensor unit and the n-th sensor unit is determined by a predetermined maximum time delay between the detection of a first signal change of a first signal of the first sensor unit and the detection of a signal change of a n-th signal of the n-th sensor unit, which signal change corresponds to the first signal change at a predetermined flow rate through the fluid-guiding line connection and the proximity of the first sensor unit and of the n-th sensor unit is predetermined in such manner that, at the predetermined flow rate, in the first signal of the first sensor unit and in the n-th signal of the n-th sensor unit signal changes each of which corresponding to each other are occurring practically free from time shift when both signals are simultaneously detected in parallel within the predetermined maximum time delay.

In medical apparatuses such as a machine for extracorporeal blood treatment, various sensor units detect data and/or signals typical of the same and output them for further processing. Against this general background, according to aspects of the invention data and/or signals of the various sensor units are to be merged so as to establish or calculate further parameter on the basis of the sensor outputs. Accordingly, especially quick signal changes are to be detectable so that operating times and/or delay times between relevant parts of the sensor outputs are to be minimized which otherwise would have to be eliminated with increased effort and in a way counter-acting the detection of quick signal changes. In other words, the drop of operating times or delay times due to flow velocity accelerates and facilitates the detection and the determination of a desired signal or parameter. In this way, operating times and delay times are no longer important when the individual sensors are disposed in direct vicinity to each other.

According to the underlying inventive idea, to this end in a drain line for used dialysis fluid plural different sensors, more exactly speaking at least one optical sensor and at least one non-optical sensor, are disposed in direct vicinity to each other, the optical sensor being capable, for example, of supplying data and/or signals for establishing the dialysis dose Kt/V and the non-optical sensor being capable of comprising a conductivity cell or conductivity probe and a temperature probe. Direct vicinity in this context is understood to be a maximum distance between sensors considered in each case at which (with dialysis fluid drained at a predetermined flow or predetermined flow rate) for example a time delay between signal outputs of the sensors considered does not exceed a predetermined or maximum and, respectively, tolerable duration.

When, for example, the inner diameter of a drain line is 5 mm, the dialysis fluid flows through the drain line at a flow rate of 500 ml/min and at a dialysis machine flows between 300 ml/min and 800 ml/min can be set, in the case of an assumed average flow of 500 ml/min in the drain line a maximum distance between two sensors amounts to 424 mm, if a time delay concerning the signals at a first sensor and a second sensor of a maximum of 1 second is to be tolerable. The possible distance increases with increasing flow through the drain line and may amount to about 679 mm at a flow of 800 ml/min. If the maximum time delay is about 1 second, in accordance with the invention the sensors are in direct vicinity to each other. Therefore, of preference a maximum distance between a first sensor and a n-th sensor of 680 mm may be predetermined, wherein further sensors may be placed between the first sensor and the n-th sensor (n-2). Optimally, moreover the sensors are disposed so closely to each other that long tube connections may be dispensed with.

In other words, it is not the maximum flow rate limiting the maximum distance but the minimum flow. For example, stating that a maximum time delay is 1 second (which means "practically free from time shift" in the sense of this disclosure) and the inner diameter of the fluid line is 5 mm, then the maximum distance is:

679 mm when the flow rate is 800 ml/min;
424 mm when the flow rate is 500 ml/min;
254 mm when the flow rate is 300 ml/min;
85 mm when the flow rate is 100 ml/min.

So far from prior art, on the one hand, a combination of measuring values of the afore-mentioned sensor units or sensors, i.e. use of the respective parameters to determine a different parameter within the scope of a measuring data merger has not been known. In other words, a combination of conductivity probe/temperature probe and optical sensor not known so far is provided for determining the dialysis dose. On the other hand, from prior art the combination of the afore-mentioned sensor units or sensors according to aspects of the invention in a drain line for used dialysis fluid, for example, has not been known. In other words, the individual sensors may already be installed at a different place, but in their position at a different place they do not enable the detection and/or determination of quick signal changes underlying here without taking signal delay times into consideration.

According to aspects of the invention, thus an advantageous and, inter alia, space-saving arrangement of the sensors within the machine, the drop of time-shifted signals due to the elimination or at least reduction of the spatial separation to such degree that flow rates and/or volumes need not be considered any longer, and a compact design avoiding undesired dead spaces are resulting.

In detail, the object is achieved by a multi-sensor device for a medical apparatus in which at least one first sensor unit and at least one n-th sensor unit are disposed at a fluid-guiding line connection along which the sensor units detect at least one variable from a flowing fluid in predetermined proximity to each other in such manner that predetermined signal portions occur and are detectable in outputs of each of the first and the n-th sensor unit practically simultaneously. Practically simultaneously preferably means that the predetermined signal portions do not exceed a predetermined maximum time delay between occurrence thereof. Advantageously, in this way signal portions in the outputs of the individual sensors that form the basis for further processing and especially a merger of measuring data to determine a further parameter to be established therefrom are sufficiently free from delay and, respectively, simultaneously detectable, and time-consuming elimination of delay times and/or operating times by calculation can be dispensed with. It is noted that the detected variable may preferably be a physical variable.

Of preference, a maximum distance between the first sensor unit and the n-th sensor unit is determined by a predetermined maximum time delay between the detection of a signal of the first sensor unit and the detection of a signal of the n-th sensor unit at a predetermined flow rate through the fluid-guiding line connection. Since the maximum distance depends on a respective flow rate through the fluid-guiding line connection, with a known flow rate a maximum distance between the first and a respective n-th sensor unit can be established and, respectively, defined by setting a time condition, for example a maximum time delay concerning the signals at the first sensor unit and the n-th sensor unit.

Of preference, the medical apparatus is a machine for extracorporeal blood treatment; the at least one sensor unit is a non-optical sensor unit; the at least one n-th sensor unit is an optical sensor unit; and the fluid-guiding line connection is a drain line for used dialysis fluid of the machine for extracorporeal blood treatment. Advantageously, such combination of sensor units detecting individually and free from delay in a machine for extracorporeal blood treatment, for example a dialysis machine, is suited for a preferred measuring data combination.

Of preference, in the multi-sensor device a housing unit is disposed at the drain line for used dialysis fluid to accommodate the at least one non-optical sensor unit and the at least one n-th optical sensor unit in the predetermined proximity to each other; the at least one non-optical sensor unit is disposed to detect and output a first signal from used dialysis fluid flowing in the drain line for used dialysis fluid; the at least one n-th optical sensor unit is disposed to detect and output a n-th signal from the used dialysis fluid flowing in the drain line for used dialysis fluid; wherein the proximity of the first sensor unit and the second sensor unit along the drain line for used dialysis fluid is predetermined such that in each of the first signal of the first sensor unit and the second signal of the second sensor unit signal portions corresponding to each other occur practically free from time shift and practically simultaneously, respectively, with a parallel simultaneous detection of both signals, i.e. they do not exceed a predetermined maximum time delay. Of advantage, the arrangement of the different sensor units in a common housing allows for modular design and degrees of freedom with respect to optimized positioning of the sensors. Since the sensor units may be sensor units through which fluid flows or sensor units through which no fluid flows, the individual sensor units may be in the form of modular components and shortest possible line passages, e.g. using short plug-in connections or fluid passages, between the individual sensor units within the housing unit and thus the largest possible vicinity of the individual sensor units relative to each other can be realized.

Of preference, in the multi-sensor device the at least one first sensor unit includes a conductivity cell for determining conductivity of used dialysis fluid and a temperature probe for measuring temperature of used dialysis fluid and for compensating the temperature of the conductivity cell; and the at least one second sensor unit includes at least one optical sensor in the form of at least one photodiode and preferably two photodetectors for determining an absorption characteristic of the used dialysis fluid. Advantageously, a combination of the measuring data output by said sensor units is suited for a preferred merger of measuring data.

Of preference, in the multi-sensor device the conductivity cell and the temperature probe are combined and installed to form a joint unit within the device. Advantageously, in this way a pre-compacting of components to be installed in as close vicinity as possible relative to each other can be realized.

Of preference, in the multi-sensor device direct vicinity of the temperature probe to the optical sensor is predetermined in such manner that a temperature detected by the temperature probe can be used to correct temperature-dependent effects in or within the optical sensor.

Of preference, in the multi-sensor device the predetermined proximity is defined so that within the multi-sensor device the respective sensor units are disposed and accommodated free from tube connections at least among each other.

Of preference, in the multi-sensor device the optical sensor is disposed directly upstream of the conductivity cell or directly downstream of the temperature probe, and more preferred upstream of the temperature probe. Preferably, in the multi-sensor device the optical sensor is disposed to be combined with a blood leakage detector.

According to the invention, the object is also achieved by a method for defining a proximity in a multi-sensor device as afore described in which positions of the individual sensors within the multi-sensor device are varied and the occurrence of predetermined signal portions in at least two signals detected by the individual sensors is detected; and those positions are defined as positions of proximity in which the predetermined signal portions will occur practically simultaneously.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
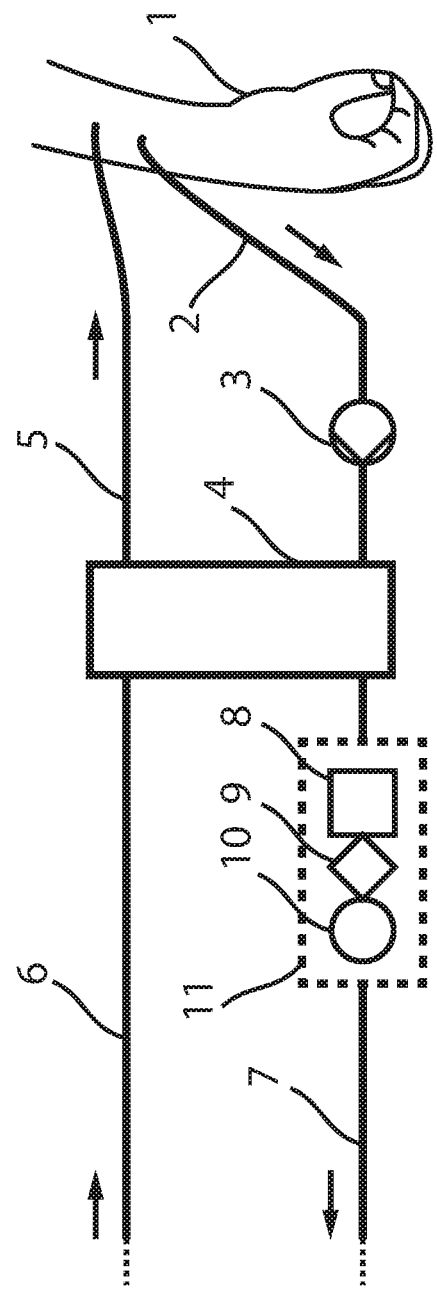
FIG. 1 shows a schematic view of a multi-sensor device according to an example embodiment.

In conformity with FIG. 1 and as shown in simplified form in the same, within the scope of extracorporeal blood treatment blood is withdrawn from a patient 1 via an arterial tubing system 2 with a delivery unit 3 and is delivered to a dialyzer 4. In the dialyzer 4 the blood of the patient is freed from substances usually to be eliminated with the urine and from excess water. Subsequently, the purified blood is returned to the patient via a venous tubing system 5. Withdrawal and return of the blood via a joint cannula is equally imaginable.

It is noted that in FIG. 1 components and parts known per se of a machine for extracorporeal blood treatment used for a detailed description in this example embodiment, such as units for proportioning the dialysis fluid or for balancing or other components which take over basic functions of a common machine for extracorporeal blood treatment, are not illustrated and will not be described herein.

In the dialyzer 4 hollow fiber capillaries (not shown) including a semi-permeable membrane (not shown) are provided. The so-called dialysis fluid which, on the one hand, absorbs substances usually to be eliminated with the urine and excess water from the blood and, on the other hand, gives off especially hydrogen carbonate for treating an acidosis of the patient 1 flows around the capillaries.

The dialysis fluid flows through a feed line 6 into the dialyzer 4. An outlet for used dialysis fluid 4a of the dialyzer 4 opens into a drain line 7 in the further course of which at least one non-optical sensor 8, 9 and at least one optical sensor 10 are arranged.

In the present example embodiment, the at least one non-optical sensor 8, 9 comprises for example a conductivity cell 8 for determining the conductivity of used dialysis fluid and a temperature probe 9 for measuring the temperature of used dialysis fluid and for temperature compensation of the conductivity cell 8.

The at least one optical sensor 10 in the present example embodiment comprises for example at least one photodiode and preferably two photodetectors and is used to determine an absorption characteristic of the used dialysis fluid.

Of preference, this is the absorbance or extinction which can be measured when the used dialysis fluid includes substances which are absorbing light. The photodiode of the optical sensor 10 for this purpose emits narrow-band light in the UV range having wavelengths preferably between 200 and 350 nm. Further preferred, light having a peak wavelength of from 275 to 295 nm is emitted. The invention is not limited to said concrete numbers of sensors and wavelengths of light used. The invention also comprises the emission and detection of plural wavelengths.

As an alternative, the optical sensor 10 may be arranged to emit light for exciting optically active substances and to subsequently measure fluorescent emissions. Further alternatively, the optical sensor 10 may be based on a laser-induced plasma spectroscopy.

As is shown in greater detail in FIG. 1, in the present example embodiment of the multi-sensor device the aforementioned sensors 8, 9 and 10 are accommodated in a common housing or a housing unit 11 and are arranged so that they are in direct vicinity to each other and preferably form a compact unit. Within the multi-sensor device specifically the conductivity cell 8 and the temperature probe 9 may further be combined and installed to form a joint unit.

In the present example embodiment, an inner diameter of the drain line 7 may be, for example, 5 mm and used dialysis fluid may flow through said drain line 7 at a flow of e.g. 500 ml/min. It is noted that the afore-mentioned values are practical values from a field realized and/or adjustable in a known dialysis machine. For example, at a known dialysis machine flows of fresh and, respectively, used dialysis fluid between 300 ml/min or less and 800 ml/min can be adjusted. A flow of 500 ml/min in this respect constitutes a mean value in the setting range of the known dialysis machine.

In the present embodiment, moreover a maximum time delay of e.g. 1 second concerning or between the signals is to be tolerable at a first sensor (for example sensor 8) and at a second sensor (for example sensor 10). Assuming an average flow of 500 ml/min in the drain line 7, a maximum distance between the first and second sensors is calculated to be 424 mm. It is noted that the maximum distance increases with an increasing flow rate through the drain line 7 and at a flow of 800 ml/min is about 679 mm.

Consequently, the direct vicinity according to the invention is given by the time delay maximally to be tolerated (e.g. 1 second) between signals of two sensors (a first sensor and a second sensor) to be considered. In other words, two sensors are provided in direct vicinity to each other when the time delay between the signals thereof does not amount to more than approx. 1 second.

In this example embodiment, therefore preferably a maximum distance between a first sensor (e.g. sensor 8) and a n-th sensor (e.g. sensor 10) of 680 mm (corresponding to the highest adjustable flow rate of 800 ml/min in this case) is defined. Between the first sensor and the n-th sensor then (n-2) further sensors (e.g. sensor 9) may be arranged, alternatively for example especially also similar and thus multiply arranged sensors which in this case for lower flow rates ensure the condition of direct vicinity while observing the time criterion, as described before. Advantageously, said n sensors are arranged so closely to each other that long tube connections are omitted.

It is understood that the invention is not limited to the numerical values and/or setting ranges afore-stated by way of example, but that appropriate ratios, relations and orders of magnitude will result also for other diameters of the drain line 7 and/or adjustable flows and/or distances and, respectively, time conditions.

The multi-sensor device according to the present example embodiment including the individual sensors 8, 9 and 10 in direct vicinity to each other enables reliable compensation of an effect of temperature and, respectively, impact of temperature on the conductivity measurement without having to take temperature losses or time-shifted signals into account.

Due to the direct and immediate vicinity of the temperature probe 9 to the optical sensor 10, moreover advantageously the (detected) temperature can be used to correct possible temperature-dependent effects in the optical sensor 10.

The arrangement of the sensors 8, 9 and 10 in proximity to each other moreover advantageously minimizes effects occurring especially due to flow-dependent time-shifted signals or signal changes. In this way, signals or signal changes can be detected, within the scope according to the invention, quasi simultaneously by the respective sensors 8, 9 and 10, and the flow of used dialysis fluid flowing through the drain line 7 may remain irrelevant, i.e. it plays no further role as regards the signals to be detected and to be processed. This is of interest especially when methods for determining relevant parameters are based on approaches of sensor merger and approaches of sensor combination.

For qualitative illustration of these facts, in the following FIG. 2 will be referred to. On the left and on the right in FIG. 2 a time curve of two signals is shown. A first signal 1 originates from a first sensor (for example the non-optical sensor 8, 9 in the present example embodiment) and a second signal 2 originates from a second sensor (for example the optical sensor 10 in the present example embodiment). Accordingly, it is understood that the first signal 1 may also originate from the optical sensor 10 and the second signal 2 may also originate from the non-optical sensor 8, 9.

Figure 2:
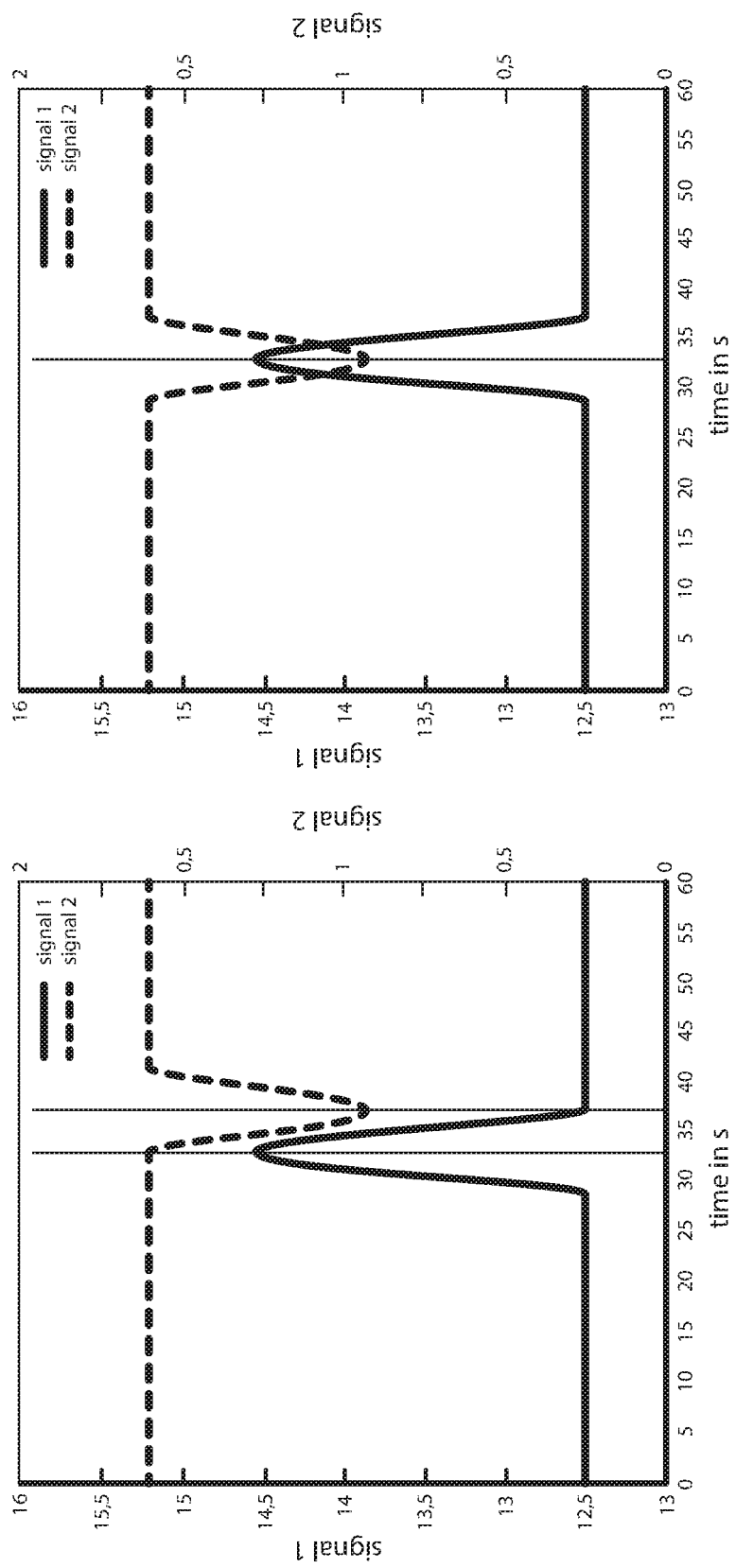
FIG. 2 shows a schematic view which, on the left side, shows a time curve of two signals of a first sensor and of a second sensor whose spatial arrangement results in time shift between extremums of the individual sensor signals, and on the right side shows a time curve of two signals of the first and second sensors in proximity of the sensors such that extremums of the individual sensor signals will appear simultaneously.

As is shown on the left side in FIG. 2 and as comparative example of a known arrangement, after detection time of e.g. about 30 s a signal change of the first signal 1 is detected by the first sensor. By way of example, a maximum or extremum of the first signal 1 occurring after about 33 s is to be of interest. A minimum or extremum in the second signal 2 of the second sensor occurs, related to the maximum of the first signal 1, only 4 s later, i.e. the two extremums of the first signal 1 and of the second signal 2 are detected shifted in time. When the flow rate and the volume between the first and second sensors are known, the time shift can be calculated therefrom. Both extremums then can be merged and unified or combined.

On the right side in FIG. 2, in conformity with the multi-sensor device according to the present embodiment equally two signal curves are shown. In this case, too, for example after a detection time of approx. 30 s a signal change of the first signal 1 is detected by the first sensor, and by way of example a maximum or extremum of the first signal 1 occurring after about 33 s is to be of interest. Directly evident, according to the example embodiment a minimum or extremum occurs in the second signal 2 of the second sensor related to the maximum of the first signal 1 practically simultaneously with the maximum of the first signal 1, i.e. the two extremums of the first signal 1 and the second signal 2 are detected practically simultaneously. The knowledge of flow rates and volumes is not required, as both extremums appear simultaneously and thus calculation of a time shift between the signals and merger of the extremums of the signals may be dropped.

Consequently, it is possible for example in a development phase of the multi-sensor device to detect, by way of a criterion such as "drop of shift calculation with sufficiently simultaneous occurrence of sensor signal extremums" by variation of sensor positions of the individual sensors in the multi-sensor device, the occurrence of extremums in at least two signals detected by sensors of the multi-sensor device and then to define those sensor positions at which the extremums occur practically or, respectively, sufficiently simultaneously as being spatially close to each other according to the invention.

Another advantage of the arrangement spatially close according to the invention consists in the fact that the arrangement of the sensors in direct vicinity to each other enables to dispense with tube connections among each other. Tube connections usually require tube olives having appropriate length at the individual components so as to be able to safely arrange the tubes there. Such connections also bear the risk of dead spaces being formed, however, which are difficult to disinfect.

For three sensors according to the present example embodiment (conductivity cell 8, temperature sensor 9 and optical sensor 10) six options of arranging the same in the flow direction within the drain line 7 are resulting. However, it may be advantageous not to separate the conductivity cell 8 and the temperature probe 9 from each other so that they are located directly next to each other in any case and to dispose the optical sensor 10 either directly upstream of the conductivity cell 8 or directly downstream of the temperature probe 9. Of preference, the optical sensor 10 is disposed next to the temperature probe 9, as sensors the data of which are to be merged should advantageously be positioned in direct vicinity to each other.

As described in the foregoing in conformity with the present example embodiment, the individual sensors 8, 9 and 10 accommodated in the housing unit 11 may form an optical sensor for determining extinction and a temperature-compensating or temperature-compensated conductivity cell. However, the invention is not limited to that, but moreover even further sensors may be accommodated.

Dialysis machines, for example, usually have an optical sensor for detecting a possible blood leakage in the drain line 7. Therefore, preferably such blood leakage detector and the optical sensor 10 may be combined with each other, as both sensors also include already related component parts (e.g. light sources, photodetectors and the like).

As described in the foregoing, in a multi-sensor device for a medical apparatus at least one first sensor unit 8, 9 and at least one second sensor unit 10 are disposed on a fluid-guiding line connection 7 along which the sensor units 8, 9, 10 detect at least one variable from a flowing fluid in predetermined proximity to each other in such manner that predetermined signal portions occur and are detectable practically simultaneously in outputs of each of the first and second sensor units. In a method for defining a proximity in such multi-sensor device, positions of the individual sensors 8, 9, 10 are varied in the multi-sensor device and the occurrence of predetermined signal portions is detected in at least two signals detected by the individual sensors 8, 9, 10, and those positions at which the predetermined signal portions occur practically simultaneously are defined as positions of proximity.

It is understood that the invention is not limited to the afore-described example embodiment, but that changes, modifications and equivalent arrangements within the scope of protection as defined according to the claims are equally comprised by the invention.

The invention claimed is:

1. A multi-sensor device for a medical apparatus, comprising:
    a first sensor unit; and
    at least one other sensor unit, the first sensor unit and the at least one other sensor unit arranged at a fluid-guiding line connection along which the first and the at least one other sensor units detect at least one variable from a flowing fluid in predetermined proximity to each sensor unit;
    wherein a maximum distance between the first sensor unit and the at least one other sensor unit is determined by a predetermined maximum time delay between the detection of a first signal change of a first signal of the first sensor unit and the detection of another signal change of another signal of the at least one other sensor unit, the other signal change corresponding to the first signal change at a predetermined flow rate through the fluid-guiding line connection; and
    wherein proximity of the first sensor unit and of the at least one other sensor unit is predetermined in such manner that, at the predetermined flow rate, in the first signal of the first sensor unit and in the other signal of the at least one other sensor unit corresponding signal changes occur without time shift when both signals are simultaneously detected in parallel within the predetermined maximum time delay.

2. The multi-sensor device according to claim 1, wherein the medical apparatus is a machine for extracorporeal blood treatment;
    the first sensor unit is a non-optical sensor unit;
    the at least one other sensor unit is an optical sensor unit; and
    the fluid-guiding line connection is a drain line for used dialysis fluid of the machine for extracorporeal blood treatment.

3. The multi-sensor device according to claim 2, further comprising:
    a housing unit arranged at the drain line for used dialysis fluid to accommodate the at least one non-optical sensor unit and the at least one other optical sensor unit in the predetermined proximity to each other;
    wherein the non-optical sensor unit is arranged to detect and to output the other signal from the used dialysis fluid flowing in the drain line for used dialysis fluid; and
    wherein the proximity of the first sensor unit and of the at least one other sensor unit along the drain line for used dialysis fluid is predetermined such that in the first signal of the first sensor unit and in the other signal of the at least one other sensor unit the corresponding signal portions occur without time shift when both signals are simultaneously detected in parallel.

4. The multi-sensor device according to claim 1, wherein:
    the first sensor unit includes a conductivity cell for determining conductivity of used dialysis fluid and a temperature probe for measuring a temperature of used dialysis fluid and for temperature compensation of the conductivity cell; and
    the at least one other sensor unit includes at least one optical sensor in the form of at least one photodiode for determining an absorption characteristic of the used dialysis fluid.

5. The multi-sensor device according to claim 4, wherein the conductivity cell and the temperature probe are combined and installed in a joint unit within the multi-sensor device.

6. The multi-sensor device according to claim 4, wherein a direct vicinity of the temperature probe to the optical sensor is predetermined such that a temperature detected by the temperature probe can be used to correct temperature-dependent effects within the optical sensor.

7. The multi-sensor device according to claim 1, wherein the predetermined proximity is defined such that within the multi-sensor device the respective sensor units are arranged and accommodated among each other free from tube connections.

8. The multi-sensor device according to claim 4, wherein the optical sensor is arranged directly upstream of the conductivity cell or directly downstream of the temperature probe.

9. The multi-sensor device according to claim 4, wherein the optical sensor is arranged to be combined with a blood leakage detector.

* * * * *